March 21, 1967 H. C. SWIM ET AL Plant Pat. 2,727
ROSE PLANT
Filed March 2, 1966
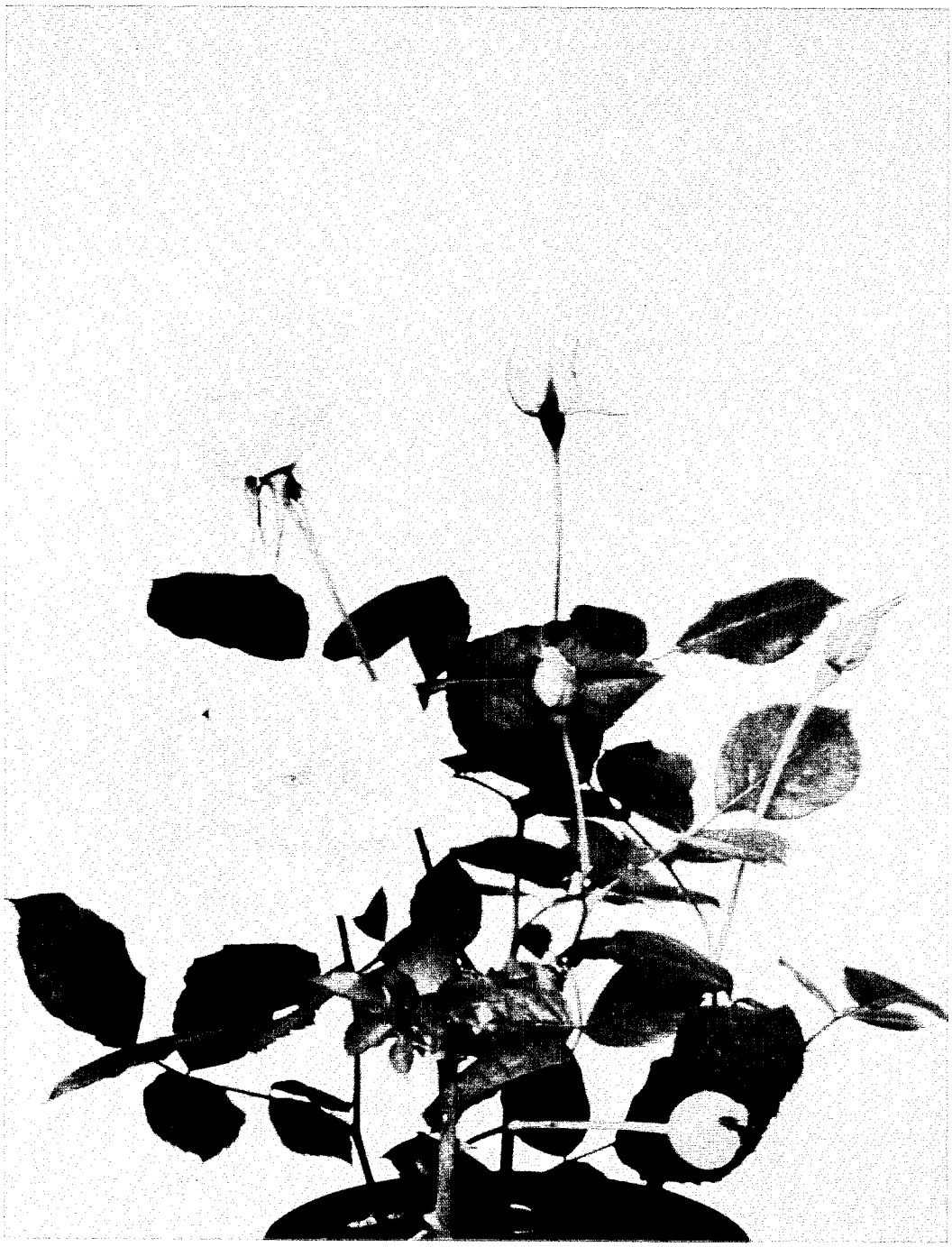
Inventors.
H. C. Swim
O. L. Weeks
By: Robb & Robb
Attorneys.

United States Patent Office

Plant Pat. 2,727
Patented Mar. 21, 1967

2,727
ROSE PLANT

Herbert C. Swim, Ontario, and O. L. Weeks, Chino, Calif., assignors to Swim and Weeks, Chino, Calif., a co-partnership Filed Mar. 2, 1966, Ser. No. 531,316
1 Claim. (Cl. Plt.—24)

The present invention relates to a new and distinct variety of rose plant of the floribunda class, which was originated by us by crossing the variety "Ophelia" (unpatented) with the variety "Circus" (Plant Patent No. 1,382).

As the result of this breeding, we have produced a new and improved rose variety having the following unique combination of characteristics which are outstanding therein and which distinguish it from its parents, as well as from all other varieties of which we are aware:

(1) The attractive color and shape of the foliage, as disclosed;

(2) Free production under glass of flowers of good petalage without material interruption during the winter season;

(3) Relatively long peduncles as compared with other yellow-flowered floribunda varieties commonly grown under glass, permitting the flowers, when wrapped in bunches, to be displayed above the leaves rather than intermixed with them;

(4) A bud form ranging from pointed to urn-shaped, said buds maturing to open flowers having a form ranging from high-centered to flat;

(5) A thick and leathery texture of the flower petals, with resultant good lasting qualities of the flowers both on the plant and when cut; and (6) A distinctive and attractive general color tonality of the flowers corresponding to near Vivid Yellow at the center with near white or yellowish-white over the outer portions when newly opened, but changing to between white and brilliant greenish-white in the three-days open flowers.

In comparison with its seed parent, "Ophelia," our new variety is classified as a floribunda rose, whereas this parent is a hybrid tea; it has many more flowers than this parent; the flowers are substantially smaller in size, but usually have from 40 to 50% more petals than the flowers of this parent; the flower petals have substantially greater substance or stiffness; the flower colors are confined to only yellow and white color tones, whereas the flowers of this parent are popularly described as salmon-flesh color, with their centers tinted with light yellow; and the flowers of the new variety have only a very slight fragrance instead of a strong fragrance as in the parent variety.

As compared with its pollen parent, "Circus," our new variety has substantially fewer and smaller thorns on the canes and branches; the flower colors are confined to only yellow and white color tones instead of being yellow marked pink, salmon and scarlet as in this parent; the flowers have only a very slight fragrance instead of the pronounced mixed fragrance of spice and tea as in this parent; the hips are, on the average, approximately half the size of those of this parent; and the hips are yellow-russet in color instead of deep orange heavily overlaid with red as those of "Circus."

Asexual reproduction of our new variety by budding, as performed at Chino, Calif., shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporated, of Baltimore, Maryland, except where general color terms of ordinary dictionary significance are obvious:

Type: Low-growing; bush; greenhouse; seedling; for cut flowers.

Class: Floribunda.

Breeding: Seedling.

*Seed parent.*—"Ophelia."

*Pollen parent.*—"Circus."

Propagation: Holds its distinguishing characteristics through succeeding propagations by budding.

*Flower*

Locality where grown and observed: Chino, California.

Flowers borne: Both singly and several to stem; on stems of normal strength and from short to medium length.

Quantity of bloom: Free, in greenhouse.

Continuity: Fairly continuous.

Fragrance: Moderately penetrating. Nature—tea.

Bud:

*Peduncle.*—Long; medium caliper; erect; with numerous small prickles and stipitate glands. Color—light yellowish-green.

*Before calyx breaks.*—Size—from medium to large for its class. Form—short; from pointed to ovoid; with a conspicuous neck; with small foliaceous appendages on the surface of the bud; usually without foliaceous parts extending beyond the tip of the bud. Color—near Brilliant Yellow Green, Plate 2.5GY 9/8.

*As calyx breaks.*—Color—near Vivid Yellow, Plate 5Y 8/12.

*As first petal opens.*—Size—large for its class. Form—from pointed to ovoid to urn-shaped. Color: outside—near Vivid Yellow, Plate 5Y 8/12 at base, fading to near white at margins and with the whitish area increasing with the unfolding of the flower; inside—Vivid Yellow, Plate 5Y 8/12, except at margins which fade to near white.

*Opening.*—Opens up well.

Bloom:

*Size (when fully open).*—Large for its class; from 2¾ inches to 3 inches.

*Petalage.*—Double, but stamens not hidden; from 30 to 45 petals, plus 6 to 10 petaloids; arranged regularly.

*Form.*—High-centered at first, but becoming flat; petals being at first loosely rolled outward, but later becoming loosely flat at maturity.

Petals:

*Texture.*—Thick; leathery.

*Appearance.*—Inside—satiny. Outside—from shiny to satiny.

*Shape.*—Outside—broadly obovate and scalloped, with apex acute and with one notch. Intermediate—obovate, with apex acute. Inside—narrowly obovate, with apex sometimes having one notch.

This description of a newly opened flower was made from a rose grown in a greenhouse during the month of November at Chino, Calif.:

*Color.*—Outer petal: outside surface—Brilliant Greenish-Yellow, Plate 7.5Y 9/8, but fading toward margin to a yellowish-white; inside surface—Vivid Yellow, Plate 5Y 8/12 at base, but changing quickly through Brilliant Greenish-Yellow, Plate 7.5Y 9/8 to a yellowish-white at margins. Intermediate petal: outside surface—Vivid Yellow, Plate 5Y 8/12 over lower half to two-thirds of petal, but fading progressively at apex with opening to a yellowish-white; inside surface—Vivid Yellow, Plate 5Y 8/12, fading toward apex until it is a yellowish-white which progressively becomes a larger faded area as the flower opens and ages. Inner petal: outside surface—Vivid Yellow, Plate 5Y 8/12; inside surface—Vivid Yellow, Plate 5Y 8/12.

This description was made from a rose that was open for three days in a greenhouse during the month of November at Chino, Calif.:

*Color.*—Outer petal: outside surface—near Brilliant Greenish-Yellow, Plate 7.5Y 9/8 over about one-third of petal at base, with remainder of petal a faintly yellowish-white; inside surface—Brilliant Greenish-Yellow, Plate 7.5Y 9/8 over a relatively small area at base, with remainder of petal near white and influenced only slightly by yellow. Inner petal: outside surface—Brilliant Greenish-Yellow, Plate 7.5Y 9/8 over about half of petal at base, with remainder a slightly yellowish-white; inside surface—Brilliant Yellow, Plate 5Y 9/9 at point of attachment, changing quickly to Brilliant Greenish-Yellow, Plate 7.5Y 9/8 progressing upward, and soon becoming near white with only a faint yellow cast.

*General color effect.*—Newly opened flower—near Vivid Yellow, Plate 5Y 8/12 in center, but near white or yellowish-white on outer part of flower. 3-days open—between white and Brilliant Greenish-Yellow, Plate 7.5Y 9/8.

*Behavior.*—Petaloids persist.

*Flower longevity.*—Cut roses grown in greenhouse and kept at living room temperatures—5 days in November.

*Reproductive organs*

Stamens: Many; arranged fairly regularly about pistils and mixed with petaloids.

Filaments: Long; most with anthers. Color—yellow.

Anthers: Medium size; all open at once or nearly so. Color—yellow-gold.

Pollen: Abundant. Color—gold.

Pistils: Many.

Styles: Uneven; short; medium caliper; loosely and unevenly bunched. Color—bright red at top beneath stigma.

Stigma: Color—translucent whitish-yellow.

Ovaries: Most enclosed in, but some protruding from calyx.

Hips: Either globular or from pear-shaped to gourd-shaped; smooth, except for russetting; walls thick and fleshy. Color—yellow russet, when mature.

Sepals: Falling before maturity; straight; from spear-shaped to curled.

Seeds: From medium size to large for class.

*Plant*

Foliage:

*Leaves.*—Compound of 3–5 leaflets; normal quantity; moderately large size; moderately leathery; semi-glossy.

*Leaflets.*—Shape—oval laterals, with terminals sometimes ovatecuneate. Apex—acute on laterals and acuminate on terminals. Base—usually round, but sometimes cuneate on terminals. Margin—simply serrate; relatively flat.

*Color.*—Mature: upper surface—normal green; under surface—grey-green, with reddish-purple overlay on midrib and between lateral veins. Young: upper surface—yellow-green, with Moderate Reddish-Brown, Plate 7.5R 3/6 on margins; under surface—reddish-brown overlay on everything except lateral veins which are green.

*Rachis (the supporting stem of the compound leaf).*—From light to medium weight. Upper side—grooved; lined with moderate number of stipitate glands. Under side—smooth, except for occasional prickles.

*Stipules.*—Short; narrow; with short points recurved toward the stem.

*Disease resistance.*—Substantially better than average resistance to powdery mildew when grown in greenhouse, as determined by comparison with many other varieties grown under comparable conditions at Chino, Calif.

Growth:

*Habit.*—Low-growing; bushy; much-branched.

*Growth.*—Moderate.

*Canes.*—Light caliper.

*Main stems.*—Color—dull olive green. Large prickles—several; medium length; straight; with short, narrow base; color—grey-brown. Small prickles—few; color—grey-brown. Hairs—none.

*Branches.*—Color—dull grey-green. Large prickles—several; medium length; straight; with short, narrow base; color—brown. Small prickles—few; color—brown. Hairs—none.

*New shoots.*—Color—near strong Yellow Green, Plate 2.5GY 6/8, with leaf margins Moderate Reddish-Brown, Plate 7.5R 3/6. Large prickles—few; medium length; straight; with short, narrow base; color—light green. Small prickles—few; color—green. Hairs—none.

We claim:

A new and distinct variety of rose plant of the floribunda class, substantially as herein shown and described, characterized particularly as to novelty by the unique combination of the attractive color and shape of the foliage, as disclosed, free production under glass of flowers of good petalage without material interruption during the winter season, relatively long peduncles as compared with other yellow-flowered floribunda varieties commonly grown under glass, permitting the flowers, when wrapped in bunches to be displayed above the leaves rather than inter-mixed with them, a bud form ranging from pointed to urn-shaped said buds maturing to open flowers having a form ranging from high-centered to flat, a thick and leathery texture of the flower petals, with resultant good lasting qualities of the flowers both on the plane and when cut, and a distinctive and attractive general color tonality of the flowers corresponding to near Vivid Yellow at the center with near white or yellowish-white over the outer portions when newly opened, but changing to between white and brilliant greenish-white in the three-days open flowers.

No references cited.

ABRAHAM G. STONE, *Primary Examiner.*

ROBERT E. BAGWILL, *Assistant Examiner.*